United States Patent [19]
Byström et al.

[11] Patent Number: 6,045,828
[45] Date of Patent: Apr. 4, 2000

[54] POWDERS FOR INHALATION

[75] Inventors: Katarina Byström, Genarp; Per-Gunnar Nilsson, Malmö, both of Sweden

[73] Assignee: Astra Aktiebolag, Sweden

[21] Appl. No.: 08/617,918

[22] PCT Filed: Dec. 20, 1995

[86] PCT No.: PCT/SE95/01560

§ 371 Date: Mar. 20, 1996

§ 102(e) Date: Mar. 20, 1996

[87] PCT Pub. No.: WO96/19199

PCT Pub. Date: Jun. 27, 1996

[30] Foreign Application Priority Data

Dec. 22, 1994 [SE] Sweden ................................. 9404466
Jun. 30, 1995 [SE] Sweden ................................. 9502369

[51] Int. Cl.$^7$ ............................. A01N 25/34; A61K 9/14
[52] U.S. Cl. ........................... 424/489; 424/404; 424/450
[58] Field of Search ................................. 424/404, 450, 424/489; 514/78

[56] References Cited

U.S. PATENT DOCUMENTS

| | | | |
|---|---|---|---|
| 4,744,989 | 5/1988 | Payne | 424/490 |
| 5,004,611 | 4/1991 | Leigh | 424/450 |
| 5,635,206 | 6/1997 | Ganter | 424/450 |

FOREIGN PATENT DOCUMENTS 9619199 6/1996 WIPO.

OTHER PUBLICATIONS

Payne et al, Characterization of Proliposomes, J. Phar. Sci. (1986), 75(4), 330–3.

Payne et al, Proliposomes: a novel solution to an old problem, J. Phar. Sci. (1986), 75(4), 325–9.

Shaw et al., "Liposomal Retention of a Modified Anti–Inflammatory Steriod" Biochem. J. 158:473–476 (1976).

*Primary Examiner*—S. Mark Clardy
*Assistant Examiner*—Kathryne E. Shelborne
*Attorney, Agent, or Firm*—Fish & Richardson P.C.

[57] ABSTRACT

A proliposome powder, said powder comprising in a single phase discrete particles of a biologically active component together with a lipid or mixture of lipids having a phase transition temperature of below 37° C. and a process for the manufacture of a proliposome powder for inhalation.

70 Claims, No Drawings

POWDERS FOR INHALATION

FIELD OF THE INVENTION

The present invention relates to proliposome powders, particularly for inhalation, a process for producing the proliposome powders, compositions containing the proliposome powders and methods for their use.

TECHNICAL BACKGROUND

Liposomes are membrane-like vesicles consisting of series of concentric lipid bilayers alternating with hydrophilic compartments. They can be made from a variety of natural and synthetic lipids such as natural and synthetic phosphoglycerolipids, sphingolipids, and digalactosylglycerolipids. One of the main uses for liposomes has been as carriers for different kinds of pharmaceutically active components, in order to improve drug delivery and to minimise side-effects of some treatments. The pharmaceutically active components can be incorporated into liposomes either by encapsulation in hydrophilic compartments of the liposome (when the active component is water-soluble), or by encapsulation into the lipid bilayers, when the active component is lipophilic.

One of the major problems associated with pharmaceutical liposomal formulations is the long-term stability. Aqueous liposome dispersions have a limited stability due to aggregation, loss of the encapsulated active component to the external phase, chemical degradation of the active component or the lipid material, etc.

These problems can to a large extent be overcome if a solid composition is used. Such a solid composition can comprise a liposome powder, i.e. a dried liposome dispersion or a proliposome powder.

The process of drying liposome dispersions has the associated risk of damage to the liposome membranes. In order to minimise this risk it is necessary to dry the liposomes in the presence of protective sugars, as described for example in WO 86/01103.

U.S. Pat. No. 4,906,476 discloses liposome formulations for the delivery of steroids by inhalation. The possibility of delivering dried liposomes as a powder aerosol using a suitable device is disclosed. Delivery by spraying from a self-contained atomiser using a propellant solvent with suspended dried liposomes in a powder, dnd by spraying dried particles into the lungs with a propellant, is also disclosed.

Liposomes as such are not present in proliposome powders, but are formed when the powder is hydrated above the phase transition temperature of the lipids. Compared with dried liposomes, proliposome powders therefore have the advantage that the risk of damage to the liposome membranes on dehydration is eliminated.

Proliposome powders have been described previously.

For example, U.S. Pat. No. 4,311,712 discloses a freeze-dried potential liposome mixture obtained by dissolving a liposome-forming amphipathic lipid and a lipid-soluble or lipid-bound biologically active compound in an organic solvent which remains solid during the freeze-drying process, and freeze-drying the solution. The potential liposome mixture may be stored and made up into an aqueous liposome preparation when desired. The biologically active compound may be any compound having a property of biological interest.

WO 90/00389 discloses a freeze-dried potential liposome mixture having an amphipathic lipid and a cyclosporin or derivative thereof, for use in possible liposome delivery of cyclosporin into cells. The freeze-dried mixture is reconstituted in aqueous medium to yield liposomes which encapsulate substantially all of the cyclosporin present in the freeze-dried mixture.

WO 92/11842 discloses a preliposomal powder which forms a suspension of liposomes containing a polyene drug such as nystatin when reconstituted with water or saline solution.

All of the above patents and applications concerning proliposome compositions are concerned with compositions which are to be hydrated prior to administration.

EP 309464 describes proliposome powder compositions which may be inhaled. The powder compositions comprise solid particles in which a biologically active component is in particulate dispersion in a lipid.

OBJECT OF THE INVENTION

We have found it advantageous to provide proliposome powders having only a single phase when delivery by inhalation is desired. Therefore it is an object of the present invention to provide such a proliposome powder.

DISCLOSURE OF THE INVENTION

The above object of the present invention is achieved in the provision according to the present invention of a proliposome powder, said powder comprising in a single phase discrete particles of a biologically active component together with a lipid or mixture of lipids having a phase transition temperature ($T_c$) of below 37° C.

The powder is particularly suitable for administration by inhalation.

The single phase powder may alternately be described as comprising a homogeneous molecular mixture of a biologically active component and a lipid or mixture of lipids having a phase transition temperature of below 37° C.

It will be understood from the terms "single phase" and "homogeneous molecular mixture" that there is no separate crystalline phase of either active component or lipid in the powder of the present invention.

The single phase powder can be inhaled directly and in situ, for example in the upper or lower respiratory system, will form liposomes in which a biologically active component is totally incorporated.

In general, any amphipathic lipid or mixture of lipids known to be suitable for preparing liposomes by known methods could be used in the present invention. The lipid or lipid mixture must have a phase-transition temperature below body temperature (37° C.) in order for th product proliposome powder to be capable of hydration under physiological conditions (i.e. in order to be able to form liposomes in the respiratory system). Phase-transition temperatures for different lipid mixtures may be estimated easily, using well-established methods, for example DSC methods—see for example J. Suurkuusk et al., Biochemistry, vol. 15, no. 7, p. 1393 (1976). In general any natural or synthetic lipid or mixture of lipids having a phase transition temperature below 37° C. is useful in the present invention.

As examples of potentially useful lipids may be mentioned natural and synthetic lipids such as natural and synthetic phosphoglycerolipids, sphingolipids, and digalactosylglycerolipids. Amongst natural lipids may be mentioned sphingolipids (SL) such as sphingomyelin (SM), ceramide and cerebroside; galactosylglycerolipids such as digalactosyldiacylglycerol (DGalDG); phosphoglycerolipids such as egg-yolk phosphatidylcholin (e-PC) and soyabean phosphatidylcholin (s-PC); and lecithins such as egg-yolk lecithin (e-lecithin) and soya-bean lecithin (s-lecithin). Amongst synthetic lipids may be mentioned dimyristoyl phosphatidylcholin (DMPC), dipalmitoyl phosphatidylcholin (DPPC), distearoyl phosphatidylcholin (DSPC), dilauryl phosphatidylcholin (DLPC), 1-myristoyl-2-palmitoyl phosphatidylcholine (MPPC), 1-palmitoyl-2-myristoyl phosphatidylcholine (PMPC), and dioleoyl phosphatidycholin (DOPC). Amongst mixtures of lipids may be mentioned the following: SM/PC, SM/Cholesterol, ePC/Cholesterol, sPC/Cholesterol, PC/PS/Cholesterol, DMPC/DPPC, DMPC/DPPC/CH, DMPC/CH, DPPC/DOPC, DPPC/DOPC/CH, DLPC/DPPC, DLPC/DPPC/CH, DLPC/DMPC, DLPC/DMPC/CH, DOPC/DSPC, DPSM/DMSM, e-lecithin/Cholesterol and s-lecithin/Cholesterol. In addition to any of the above there may be included a charged lipid such as dimyristoyl phosphatidylglycerol (DMPG), diphospalmitoyl phosphatidylglycerol (DPPG), dimyristoyl phosphatidic acid (DMPA), dipalmitoyl phosphatidic acid (DPPA) or stearylamine (SA).

Lipids of particular interest in the present invention are DPPC and/or DMPC. A mixture of DPPC and DMPC containing at least 10% (w/w) DMPC is preferred, for example 10–50% DMPC. Especially preferred is a mixture of DPPC and DMPC containing in addition at least one charged lipid sich as DMPG, DPPG, DMPA or SA, for example in an amount of up to 5% (w/w). Other preferred mixtures include DPSM and DMSM optionally containing at least one charged lipid, and mixtures of cholesterol with either e-lecithin or s-lecithin, optionally containing at least one charged lipid, and having a $T_c$ of less than 37° C. Other mixtures can be selected easily by a person skilled in the art with reference for example to Gregor Cevc, Phospholipids Handbook, Marcel Dekker, New York (1993) pp 427–435.

The active component preferably has a molecular structure which can be incorporated into the lipid bilayers, to aid encapsulation in the liposomes during hydration. An example of such is a fatty acid ester having a long hydrocarbon chain sufficient to act as hydrophobic anchor.

Suitable active components can be identified readily by a person skilled in the art and may include for example antiinflammatory and bronchorelaxing drugs as well as antihistamines, cyclooxygenase inhibitors, leukotriene synthesis inhibitors, leukotriene antagonists, phospholipase-A2 (PLA2) inhibitors, platelet aggregating factor (PAF) antagonists and prophylactics of asthma. Antiarrhythmic drugs, tranquilisers, cardiac glycosides, hormones, antihypertensive drugs, antidiabetic, antiparisitic and anticancer drugs, sedatives, analgesic drugs, antibiotics, antirheumatic drugs, immunotherapies, antifungal drugs, antihypotension drugs, vaccines, antiviral drugs, proteins, peptides and vitamins, may also be of interest.

Specifically, glucocorticosteroids such as budesonide, dexamethasone, bethamethasone, fluocinolone, flumethasone, triamcinolone acetonide, flunisolide, beclomethasone and 16, 17-acetals of pregnane derivatives and compounds derived therefrom; and β-2 agonists such as terbutaline, salmeterol, salbutamol, formoterol, fenoterol, clenbuterol, procaterol, bitolterol, and broxaterol may be useful in the present invention. The active component may also be a mixture of pharmaceutically active substances; for example a mixture of a glucocortico-steroid with a bronchodilator such as formoterol, salmeterol, terbutaline or salbutamol, may be useful. For the avoidance cf doubt, where a reference to any active component is made herein, said reference is intended to include a reference to pharmaceutically acceptable esters, salts, and hydrates thereof.

Where the active component is a steroid it is preferably a steroid ester.

The active component is preferably a steroid, preferably a steroid which is esterified in the 21-position with a fatty acid of at least 8, for example at least 10 or at least 12 carbon atoms. The fatty acid may have, for example, up to 24 carbon atoms, for example up to 20 carbon atoms or up to 18 carbon atoms. More preferably, the active component is a steroid-21-palmitate, myristate, laurate, caprate, caprylate or stearate. The most preferred active component according to the invention is the compound (22R)-16α,17α-butylidenedioxy-6α,9α-difluoro-11β-hydroxy-21-palmitoyloxypregn-4-ene-3,20-dione, i.e., rofleponide palmitate.

Where the active component is an ester it must be hydrolysed to the active principal. Surprisingly, the single phase proliposome powder of the present invention facilitates the necessary hydrolysis in situ, whereas esters in the crystalline state will not be hydrolysed.

Where delivery by inhalation is desired, as much as possible of the proliposome powder of the present invention should consist of particles having a diameter of less than 10 microns, for example 0.01–10 microns or 0.1–6 microns, for example 0.1–5 microns, or agglomerates of said particles. Preferably at least 50% of the powder consists of particles within the desired size range. For example at least 60%, preferably at least 70%, more preferably at least 80% and most preferably at least 90% of the powder consists either of particles within the desired size range or of agglomerates of said particles.

The proliposome powders of the present invention need not contain other ingredients. However pharmaceutical compositions containing the powders of the present invention may also include other pharmaceutically acceptable additives such as pharmaceutically acceptable adjuvents, diluents and carriers. These may be added to the proliposome composition after any micronisation, or before any micronisation provided that the solvent has been completely removed. Any carrier is preferably a crystalline, hydrophilic substance. A preferred carrier is crystalline lactose monohydrate. Other suitable carriers include glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, and betaine.

The amount of additives present in the formulation may vary over a very wide range. In some circumstances little or no additive may be required, whereas for example it is often preferable to dilute a powder with additive, in order to improve the powder properties for use in an inhaler. In the latter case, for example, at least 50%, for example at least 70% or at least 80% of the formulation may be made up of additives, the remainder being the proliposome powder. The percentage of additives may also be dependant on the potency of the biologically active compound and the optimal amount of powder for inhalation.

Where an additive, for example a carrier is present, the entire composition may be in the form of particles of a size within the respirable particle size range. Alternatively the carrier may comprise coarser particles, of for example mass median diameter greater than 20 microns, or it may comprise agglomerates of the smaller particles, the agglomerates having a mass median diameter of for example greater than 20 microns, so that in either case an ordered mixture of proliposome and carrier is formed.

A further object of the present invention is the provision of a process for the preparation of the proliposome powder of the present invention, i.e. a process which yields the proliposome powder in a single phase.

Accordingly, the present invention also provides a process for the preparation of a proliposome powder for inhalation, comprising dissolving a lipid or mixture of lipids and a lipophilic biologically active component in a solvent, said lipid or mixture of lipids having a phase transition temperature below 37° C.; obtaining a crystalline solvent matrix and a single lipid phase in its glassy state by freezing the solution, said freezing being carried out at a temperature below the phase transition temperature of the lipid phase; and evaporating the frozen solvent at a temperature below the phase transition temperature of the lipid phase.

Freezing of the solution and solvent evaporation may be effected by conventional methods, for example in a conventional freeze-drier. For example the solution of lipids and biologically active component may be poured onto the shelves of a freeze-drier and the temperature lowered to freeze the solution. Solvent evaporation may then be achieved for example by lowering the pressure in the freeze-drying chamber; the resulting powder may be scraped from the shelves of the chamber and optionally passed through a sieve.

The freeze-dried powder may if necessary be subjected to further processing in order to obtain particles within the respirable particle size range; for example the freeze-dried powder may be micronised to give respirable particles, for example using an air jet mill.

The freezing of the solution of biologically active component and lipids is carried out in a manner which produces a single lipid phase in the frozen solvent matrix. The production of a single lipid phase is controlled by the final temperature and the rate of freezing of the solution; the optimum rate of freezing of any particular solution will be somewhere between the time necessary for crystallisation of the solvent in question and the time necessary for crystallisation of the lipids and active component and may be determined by a person skilled in the art, simply by trial and error. The optimal final temperature should be 10–20° C. below the glass transition temperature of the lipid phase. For example a powder X-ray method may be used to monitor crystallinity and a differential scanning calorimeter may be used for monitoring the degree of incorporation of biologically active component into the liposomes after hydration.

The solvent must have the capacity to dissolve the lipids and the biologically active component completely since it is essential that all the components are in solution prior to freezing in order to avoid precipitation or phase-separation which will give rise to a powder with more than one phase. In addition the solvent should be toxicologically acceptable, have an appropriate freezing point and preferably a high vapour pressure. The solvent may be for example an organic solvent, for example an alcohol, or a mixture of aqueous and organic solvents. The preferred solvent for use in the present invention is tertiary butanol.

The powder may optionally be agglomerated into small spheres, in order to control the cohesiveness of the powder. The spheres should preferably be not larger than 1 mm in diameter; spheres larger than this may be removed for example by sieving. Any agglomerates should be friable, so that they may easily be deagglomerated for example in a powder inhaler.

The proliposome powder of the present invention is useful for the local or systemic treatment of diseases and may be administered for example via the upper and lower respiratory tract, including by the nasal route. As such the present invention also provides said proliposome powder for use in therapy; the use of the proliposome powder in the manufacture of a medicament for the treatment of diseases via the respiratory tract; and a method for the treatment of a patient in need of therapy, comprising administering to said patient a therapeutically effective amount of the proliposome powder of the present invention.

For example the proliposome powder of the present invention may be used in the treatment of inflammatory diseases in the respiratory tract, for example asthma, rhinitis, alveolitis, bronchiolitis and bronchitis.

Administration to the respiratory tract may be effected for example using a dry powder inhaler or a pressurised aerosol inhaler.

Suitable dry powder inhalers include dose inhalers, for example the single dose inhaler known by the trade mark Monohaler® and multi-dose inhalers, for example a multi-dose, breath-actuated dry powder inhaler such as the inhaler known by the trade mark Turbuhaler®.

While the proliposome powder of the present invention is particularly adapted for administration by inhalation, it may also be included in formulations adapted for other forms of delivery. For example oral, topical and injectable formulations may be prepared, for use in the treatment of for example inflammatory joint diseases, for example arthritis, skin diseases, and intestinal bowel diseases.

The following Examples are intended to illustrate, but not limit, the scope of the invention.

EXAMPLE 1

Rofleponide palmitate (10 parts), DPPC (63 parts), DMPC (24 parts) and NaDPPG (3 parts) were dissolved in tertiary butanol (1300 parts) at 80° C. The solution was poured onto the shelves of a freeze-dryer cooled to −35° C. The solution had reached this temperature after about 30 minutes; the pressure in the freeze-dryer was then reduced in order to induce sublimation of the solvent. While the rate of sublimation could be adjusted by decreasing the pressure and increasing the temperature, the temperature throughout the process was not allowed to exceed −10° C. Freeze-drying was continued until all the solvent had been removed. The resulting powder was scraped from the shelves of the freeze-dryer and passed through a sieve.

This powder was micronised in an air jet mill to a powder particle size of less than 5 $\mu$m. The micronised powder was mixed with lactose monohydrate (20 parts powder: 80 parts lactose monohydrate) by a sieving process and the mixture further homogenised by micronising at low pressure, in a jet mill.

The powder mixture was agglomerated into spheres no larger than 1 mm, using standard techniques. Larger spheres were removed by sieving. The agglomerated powder was filled into a Turbuhaler® dry powder inhaler.

EXAMPLE 2

The procedure of Example 1 was repeated with freezing times of 6 hours, 17 hours and 24 hours.

COMPARATIVE EXAMPLE

The lipids and active component of Example 1 are simply dry mixed together. The resultant powder is a multi-phase system comprising separate particles of the active component and of the lipids.

EXAMPLE 3

The procedure of Example 1 is repeated using the following lipid mixtures having a phase transition temperature below 37° C.:

DPSM/DPSM
e-Lecithin/Cholesterol
s-Lecithin/Cholesterol

EXAMPLE 4

The procedure of Example 1 is repeated with the following active components:
  rofleponide-21-myristate
  rofleponide-21-laurate
  rofleponide-21-caprate
  rofleponide-21-caprylate
  rofleponide-21-stearate Powder Analysis X-ray powder diffraction carried out on the powder mixture of Examples 1 and 2 showed that no crystalline state was present in the powder. The powder of the Comparative Example contained the active component in the crystalline state.

Incorporation of Active Component into the Liposomes

The proliposome powders of Examples 1 and 2 were hydrated and the degree of incorporation of the active component was measured using differential scanning calorimetry methods. The DSC showed that the active component was fully incorporated into the liposomes. DSC carried out on the powder of the Comparative Example showed substantially no incorporation of the active component into the liposome.

Ester Hydrolysis

The degree of hydrolysis of the proliposome powder of Example 1 and the Comparative Example to the active principal was investigated. The proliposome powders of Examples 1 and 2 and the Comparative Example (50 µM of the steroid ester in each case) were hydrated with water and heated to 50° C. for 15 minutes. Thereafter the samples were incubated at 37° C. in the presence of porcine pancreas lipase (2 mg/ml) in a buffer (1 mM EDTA, 80 mM KCl, 10 mM HEPES, pH 7.4) and periodically sonicated for varying lengths of time of up to 120 minutes. The samples were analysed by HPLC methods to determine how much of the ester had been hydroysed to the active principal.

94% of the proliposome powder of Example 1 was hydrolysed to the active principal, compared with just 2% of the powder of the Comparative Example.

Pharmacological Studies

Anti-oedema efficacy was determined using the Sephadex model on rats as described by L. Källström et al, in Agents and Actions 17(3/4) 355 (1985).

Samples of the powders of Example 1 and the Comparative Example were suspended in cold saline and given by intratracheal injection to the left lung of male Sprague-Dawley rats. After one hour an inflammation process was provoked by intratracheal instillation of Sephadex beads (5 mg/kg) to both left and right lungs. The resulting interstitial oeadema was quantified after 20 hours by determining the weight of the right and left lungs. The decrease in lung weight was taken to be indicative of the pharmacological effect of the powders. The lung weight of the rats treated with the proliposome powder of Example 1 had decreased 40 times more than the lung weight of the rats treated with the powder of the Comparative Example: that is, the efficacy of the proliposome powder according to the invention was 40 times greater than the efficacy of the powder of the Comparative Example.

Inhalation Studies

Beagle dogs were anaesthetised, intubated, and exposed to a powder aerosol of the formulation of Example 1 or of the Comparative Example. The aerosol was generated from a powder tablet using a Wright Dust Feed apparatus operated at 1800 rpm. Aerosol concentration (Casella 950 AMS), tidal volume, inspired tidal volume and breathing frequency were recorded during inhalation. The target inhaled dose was 25 µg rofleponide palmitate/kg body weight. Plasma samples were taken regularly following inhalation. Bioavailability was calculated by comparison with plasma concentrations of rofleponide following intravenous administration. The bioavailability of rofleponide following administration of the powder according to Example 1 was close to 100%, whereas the bioavailability of rofleponide following administration of the powder of the Comparative Example was not measurable.

What is claimed is:

1. A pharmaceutical composition comprising a proliposome powder and a crystalline and hydrophilic pharmaceutically acceptable carrier, said proliposome powder comprising discrete particles consisting of a single phase comprising (1) a biologically active component and (2) a lipid or mixture of lipids having a phase transition temperature of below 37° C.

2. A pharmaceutical composition as claimed in claim 1, wherein the proliposome powder comprises one or more lipids selected from the group consisting of natural phosphoglycerolipids, synthetic phosphoglycerolipids, sphingolipids and digalactosylglycerolipids.

3. A pharmaceutical composition as claimed in claim 1, wherein the proliposome powder comprises a mixture of lipids selected from the group of mixtures consisting of sphingomyelin/phosphatidylcholine, sphingomyelin/cholesterol, egg-yolk phosphatidylcholine/cholesterol, soybean phosphatidylcholine/cholesterol, phosphatidylcholine/phosphatidylserine/cholesterol, dimyristoyl phosphatidylcholine/dipalmitoyl phosphatidylcholine, dimyristoyl phosphatidylcholine/dipalmitoyl phosphatidylcholine/cholesterol, dimyristoyl phosphatidylcholine/cholesterol, dipalmitoyl phosphatidylcholine/dioleoyl phosphatidylcholine, dipalmitoyl phosphatidylcholine/dioleoyl phosphatidylcholine/cholesterol, dilauryl phosphatidylcholine/dipalmitoyl phosphatidylcholine, dilauryl phosphatidylcholine/dipalmitoyl phosphatidylcholine/cholesterol, dilauryl phosphatidylcholine/dimyristoyl phosphatidylcholine, dilauryl phosphatidylcholine/dimyristoyl phosphatidylcholine/cholesterol, and dioleoyl phosphatidylcholine/distearoyl phosphatidylcholine.

4. A pharmaceutical composition as claimed in claim 1, wherein the proliposome powder comprises dipalmitoyl phosphatidylcholine or dimyristoyl phosphatidylcholine, or a mixture of dipalmitoyl phosphatidylcholine and dimyristoyl phosphatidylcholine.

5. A pharmaceutical composition as claimed in claim 4, wherein the proliposome powder comprises a mixture of lipids at least 10% by weight of which is dimyristoyl phosphatidylcholine.

6. A pharmaceutical composition as claimed in claim 1, wherein the proliposome powder includes a charged lipid.

7. A pharmaceutical composition as claimed in claim 6, wherein the charged lipid is selected from the group consisting of dimyristoyl phosphatidylglycerol, dipalmitoyl phosphatidylglycerol, dimyristoyl phosphatidic acid and stearylamine.

8. A pharmaceutical composition as claimed in claim 1, wherein the active component is selected from the group consisting of antiinflammatory drugs, bronchorelaxing drugs, antihistamines, cyclooxygenase inhibitors, leukotriene antagonists, PLA2 inhibitors, PAF antagonists and prophylactics of asthma.

9. A pharmaceutical composition as claimed in claim 1, wherein the active component comprises a glucocorticosteroid.

10. A pharmaceutical composition as claimed in claim 1, wherein the active component comprises a β-2 agonist.

11. A pharmaceutical composition as claimed in claim 1, wherein the active component comprises a steroid which is esterified in the 21 position with a fatty acid of at least 8 carbon atoms.

12. A pharmaceutical composition as claimed in claim 1, wherein the active component comprises a steroid which is esterified in the 21 position with a fatty acid of at least 10 carbon atoms.

13. A pharmaceutical composition as claimed in claim 1, wherein the active component comprises a steroid which is esterified in the 21 position with a fatty acid of at least 12 carbon atoms.

14. A pharmaceutical composition as claimed in claim 1, wherein the active component comprises a steroid-21-palmitate.

15. A pharmaceutical composition as claimed in claim 1, wherein the active component comprises rofleponide palmitate.

16. A pharmaceutical composition as claimed in claim 1, wherein at least 50% of the proliposome powder consists of particles having a diameter of less than 10 microns.

17. A pharmaceutical composition as claimed in claim 1, wherein at least 60% of the proliposome powder consists of particles having a diameter of less than 10 microns.

18. A pharmaceutical composition as claimed in claim 1, wherein at least 70% of the proliposome powder consists of particles having a diameter of less than 10 microns.

19. A pharmaceutical composition as claimed in claim 1, wherein at least 80% of the proliposome powder consists of particles having a diameter of less than 10 microns.

20. A pharmaceutical composition as claimed in claim 1, wherein at least 90% of the proliposome powder consists of particles having a diameter of less than 10 microns.

21. A pharmaceutical composition as claimed in claim 1, wherein at least 50% of the proliposome powder consists of particles having a diameter of 0.01–10 microns.

22. A pharmaceutical composition as claimed in claim 1, wherein at least 50% of the proliposome powder consists of particles having a diameter of 0.1–6 microns.

23. A pharmaceutical composition as claimed in claim 1, wherein at least 50% of the proliposome powder consists of particles having a diameter of 0.1–5 microns.

24. A pharmaceutical composition as claimed in claim 1, comprising agglomerated particles.

25. A pharmaceutical composition as claimed in claim 1, wherein the carrier is crystalline lactose monohydrate.

26. A pharmaceutical composition as claimed in claim 1, wherein the carrier is selected from the group consisting of glucose, fructose, galactose, trehalose, sucrose, maltose, raffinose, maltitol, melezitose, stachyose, lactitol, palatinate, starch, xylitol, mannitol, myoinositol, and hydrates thereof, and amino acids.

27. A pharmaceutical composition as claimed in claim 1, wherein the carrier comprises particles of mass median diameter greater than 20 microns.

28. A pharmaceutical composition as claimed in claim 1, wherein the carrier comprises particles of mass median diameter less than 10 microns or agglomerates of said particles.

29. A process for the manufacture of a proliposome powder, comprising dissolving a lipid or mixture of lipids and a lipophilic biologically active component in a solvent, said lipid or mixture of lipids having a phase transition temperature of below 37° C.; obtaining a crystalline solvent matrix and a single lipid phase in its glassy state by freezing the solution, said freezing being carried out at a temperature below the phase transition temperature of the lipid phase; and evaporating the frozen solvent at a temperature below the phase transition temperature of the lipid phase to obtain a freeze-dried proliposome powder.

30. A process as claimed in claim 29, additionally comprising the step of micronising the freeze-dried powder to obtain particles within the respirable particle size range.

31. A process as claimed in claim 29, wherein freezing and solvent evaporation are effected in a freeze-drier.

32. A process as claimed in claim 29, wherein the solvent comprises an organic solvent.

33. A process as claimed in claim 29, wherein the solvent comprises an alcohol.

34. A process as claimed in claim 29, wherein the solvent comprises tertiary butanol.

35. A process as claimed claim 29, additionally comprising the step of agglomerating the powder particles into spheres of diameter 1 mm or less.

36. A method of treating a patient in need of therapy with a given biologically active compound, comprising administering to said patient, via inhalation, a therapeutically effective amount of a pharmaceutical composition comprising a proliposome powder and a crystalline and hydrophilic pharmaceutically acceptable carrier, said proliposome powder comprising discrete particles consisting of a single phase comprising (1) the given biologically active compound and (2) a lipid or mixture of lipids having a phase transition temperature of below 37° C.

37. A dry powder inhaler device containing a pharmaceutical composition as claimed in claim 1.

38. A dry powder inhaler device as claimed in claim 37, wherein the inhaler is a single dose inhaler.

39. A dry powder inhaler device as claimed in claim 37, wherein the inhaler is a multi dose inhaler.

40. A method as claimed in claim 36, wherein said powder comprises one or more lipids selected from the group consisting of natural and synthetic phosphoglycerolipids, sphingolipids and digalactosylglycerolipids.

41. A method as claimed in claim 36, wherein said active compound is selected from the group consisting of antiinflammatory drugs, bronchorelaxing drugs, antihistamines, cyclooxygenase inhibitors, leukotriene antagonists, PLA2 inhibitors, PAF antagonists and prophylactics of asthma.

42. A method as claimed in claim 36, wherein said active compound is a glucocorticosteroid.

43. A method as claimed in claim 36, wherein said active compound is a β-2 agonist.

44. A method as claimed in claim 36, wherein said active compound is a steroid which is esterified in the 21 position with a fatty acid of at least 8 carbon atoms.

45. A method as claimed in claim 36, wherein said active compound is rofleponide palmitate.

46. A method as claimed in claim 36, wherein at least 50% of the powder consists of particles having a diameter of less than 10 microns.

47. A method as claimed in claim 36, wherein at least 90% of the powder consists of particles having a diameter of 0.1–6 microns.

48. A method as claimed in claim 36, wherein the powder comprises a mixture of lipids selected from the group of mixtures consisting of sphingomyelin/phosphatidylcholine, sphingomyelin/cholesterol, egg-yolk phosphatidylcholine/ cholesterol, soybean phosphatidylcholine/cholesterol, phosphatidylcholine/phosphatidylserine/cholesterol, dimyristoyl phosphatidylcholine/dipalmitoyl phosphatidylcholine, dimyristoyl phosphatidylcholine/dipalmitoyl phosphatidylcholine/cholesterol, dimyristoyl phosphatidylcholine/cholesterol, dipalmitoyl phosphatidylcholine/dioleoyl phosphatidylcholine, dipalmitoyl phosphatidylcholine/dioleoyl phosphatidylcholine/cholesterol, dilauryl phosphatidylcholine/dipalmitoyl phosphatidylcholine, dilauryl phosphatidylcholine/dipalmitoyl phosphatidylcholine/cholesterol, dilauryl phosphatidylcholine/dimyristoyl phosphatidylcholine, dilauryl phosphatidylcholine/dimyristoyl phosphatidylcholine/cholesterol, and dioleoyl phosphatidylcholine/distearoyl phosphatidylcholine.

49. A method as claimed in claim 36, wherein the powder comprises a mixture of lipids at least 10% by weight of which is dimyristoyl phosphatidylcholine.

50. A process as claimed in claim 29, wherein said biologically active component comprises rofleponide palmitate.

51. A process for the manufacture of a powder mixture, the process comprising:
    dissolving a lipid or mixture of lipids and a lipophilic, biologically active component in a solvent, said lipid or mixture of lipids having a phase transition temperature of below 37° C.;
    obtaining a crystalline solvent matrix and a single lipid phase in its glassy state by freezing the solution, said freezing being carried out at a temperature below the phase transition temperature of the lipid phase;
    evaporating the frozen solvent at a temperature below the phase transition temperature of the lipid phase to obtain a freeze-dried proliposome powder, wherein the proliposome powder comprises discrete particles consisting of a single phase comprising (1) the biologically active component and (2) the lipid or mixture of lipids; and
    adding to the proliposome powder a crystalline and pharmaceutically acceptable carrier to produce a powder mixture.

52. The process of claim 56, further comprising micronising the powder mixture to obtain particles within a respirable particle size range.

53. The process of claim 51, further comprising the step of agglomerating the particles into spheres having a diameter of 1 mm or less.

54. A proliposome powder comprising discrete particles having a single phase comprising (1) rofleponide palmitate and (2) a lipid or mixture of lipids having a phase transition temperature of below 37° C.

55. The proliposome powder as claimed in claim 54, wherein the proliposome powder comprises one or more lipids selected from the group consisting of natural phosphoglycerolipids, synthetic phosphoglycerolipids, sphingolipids and digalactosylglycerolipids.

56. The proliposome powder as claimed in claim 54, wherein the proliposome powder comprises a mixture of lipids selected from the group of mixtures consisting of sphingomyelin/phosphatidylcholine, sphingomyelin/cholesterol, egg-yolk phosphatidylcholine/cholesterol, soybean phosphatidylcholine/cholesterol, phosphatidylcholine/phosphatidylserine/cholesterol, dimyristoyl phosphatidylcholine/dipalmitoyl phosphatidylcholine, dimyristoyl phosphatidylcholine/dipalmitoyl phosphatidylcholine/cholesterol, dimyristoyl phosphatidylcholine/cholesterol, dipalmitoyl phosphatidylcholine/dioleoyl phosphatidylcholine, dipalmitoyl phosphatidylcholine/dioleoyl phosphatidylcholine/cholesterol, dilauryl phosphatidylcholine/dipalmitoyl phosphatidylcholine, dilauryl phosphatidylcholine/dipalmitoyl phosphatidylcholine/cholesterol, dilauryl phosphatidylcholine/dimyristoyl phosphatidylcholine, dilauryl phosphatidylcholine/dimyristoyl phosphatidylcholine/cholesterol, and dioleoyl phosphatidylcholine/distearoyl phosphatidylcholine.

57. The proliposome powder as claimed in claim 54, wherein the proliposome powder comprises dipalmitoyl phosphatidylcholine or dimyristoyl phosphatidylcholine, or a mixture of dipalmitoyl phosphatidylcholine and dimyristoyl phosphatidylcholine.

58. The proliposome powder as claimed in claim 54, wherein the proliposome powder comprises a mixture of lipids at least 10% by weight of which is dimyristoyl phosphatidylcholine.

59. The proliposome powder as claimed in claim 54, wherein the proliposome powder comprises a charged lipid.

60. The proliposome powder as claimed in claim 59, wherein the charged lipid is selected from the group consisting of dimyristoyl phosphatidylglycerol, dipalmitoyl phosphatidylglycerol, dimyristoyl phosphatidic acid and stearylamine.

61. The proliposome powder as claimed in claim 54, wherein at least 50% of the proliposome powder consists of particles having a diameter of less than 10 microns.

62. The proliposome powder as claimed in claim 54, wherein at least 60% of the proliposome powder consists of particles having a diameter of less than 10 microns.

63. The proliposome powder as claimed in claim 54, wherein at least 70% of the proliposome powder consists of particles having a diameter of less than 10 microns.

64. The proliposome powder as claimed in claim 54, wherein at least 80% of the proliposome powder consists of particles having a diameter of less than 10 microns.

65. The proliposome powder as claimed in claim 54, wherein at least 90% of the proliposome powder consists of particles having a diameter of less than 10 microns.

66. The proliposome powder as claimed in claim 54, wherein the particles have a diameter of 0.01–10 microns.

67. The proliposome powder as claimed in claim 54, wherein the particles have a diameter of 0.01–6 microns.

68. The proliposome powder as claimed in claim 54, wherein the particles have a diameter of 0.01–5 microns.

69. The proliposome powder as claimed in claim 54, comprising agglomerated particles.

70. A dry powder inhaler device containing the proliposome powder of claim 54.

* * * * *